United States Patent [19]

Wooden et al.

[11] Patent Number: 5,202,454
[45] Date of Patent: Apr. 13, 1993

[54] PROCESS FOR THE MANUFACTURE OF 1-BROMOALKYL HYDROCARBYL CARBONATES

[75] Inventors: Gary Wooden, Mennecy; Gérard Sennyey, Saint-Aubin; Jean-Pierre Senet, Herbeauvilliers-Buthiers, all of France

[73] Assignee: Societe Nationale Des Poudres Et Explosifs, Paris, France

[21] Appl. No.: 794,842

[22] Filed: Nov. 21, 1991

Related U.S. Application Data

[63] Continuation of Ser. No. 427,916, Oct. 24, 1989, abandoned, which is a continuation of Ser. No. 298,269, Jan. 17, 1989, abandoned, which is a continuation of Ser. No. 71,917, Jul. 10, 1987, abandoned.

[30] Foreign Application Priority Data

Jul. 11, 1986 [FR] France ............................. 86 10185

[51] Int. Cl.⁵ ............................................. C07C 69/96
[52] U.S. Cl. .................................... 558/260; 558/270; 558/271; 558/275
[58] Field of Search ................ 558/270, 271, 275, 260

[56] References Cited

U.S. PATENT DOCUMENTS

| | | |
|---|---|---|
| 2,553,518 | 5/1951 | Lake et al. |
| 4,426,391 | 1/1984 | Alexander et al. ............... 560/40 X |
| 4,697,032 | 9/1987 | Malfroot et al. .................... 558/270 |

FOREIGN PATENT DOCUMENTS

| | | |
|---|---|---|
| 54512 | 6/1982 | European Pat. Off. |
| 108547 | 5/1984 | European Pat. Off. |
| 185578 | 6/1986 | European Pat. Off. |
| 2628410 | 1/1978 | Fed. Rep. of Germany |
| 2387988 | 11/1978 | France |
| 2532933 | 3/1984 | France |
| 2559764 | 8/1985 | France |
| 2573756 | 1/1987 | France |
| 2123821 | 2/1984 | United Kingdom |

OTHER PUBLICATIONS

Kirk–Othmer, Encyclopedia of Chemical Technology, 2nd revised edition, pp. 775 and 779, 1964.

*Primary Examiner*—Jose G. Dees
*Assistant Examiner*—Joseph M. Conrad, III
*Attorney, Agent, or Firm*—Burns, Doane, Swecker & Mathis

[57]. ABSTRACT

The invention relates to a new process for the preparation of 1-bromoalkyl hydrocarbyl carbonates.

The carbonates according to the invention are prepared by reacting an alpha-chlorinated carbonate of formula $$R_1-\underset{\underset{Cl}{|}}{CH}-O-\underset{\underset{O}{\|}}{C}-O-R_2$$

with an anhydrous brominated compound of formula ZBr in which Z represents hydrogen, the group $(CH_3)_3Si$-, the group $$CH_3-\underset{\underset{O}{\|}}{C}-$$

or bromine if $R_2$ is other than an aromatic radical, in the presence of a catalyst chosen from the group consisting of heteroaromatic amines, quaternary ammonium or phosphonium halides, hexasubstituted guanidinium halides, alkaline earth metal halides or alkali metal halides in combination with a complexing agent for their cation.

The carbonates according to the invention find their preferential applications as blocking agents for some antibiotics or as agents for the synthesis of phosphorus-containing carbonates which can be used as insecticides.

21 Claims, No Drawings

PROCESS FOR THE MANUFACTURE OF 1-BROMOALKYL HYDROCARBYL CARBONATES

This application is a continuation of application Ser. No. 07/427,916, filed Oct. 24, 1989, now abandoned which is a continuation of aplication Ser. No. 07/298,269, filed Jan. 17, 1989, now abandoned, which in turn is a continuation of application Ser. No. 07/071,917, filed Jul. 10, 1987, now abandoned.

The invention relates to a new process for the preparation of 1-bromoalkyl hydrocarbyl carbonates. The invention also relates to new 1-bromoalkyl hydrocarbyl carbonates.

Very few alpha-brominated carbonates are known because the preparation thereof had remained difficult until recent years.

It is possible to prepare 1-bromoethyl ethyl carbonate by reacting a 1-bromoethyl haloformate with ethanol according to the reaction scheme:

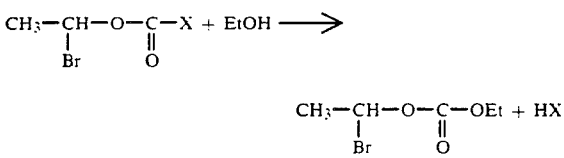

X representing chlorine or bromine.

The difficulty of this process lies in the preparation of the starting haloformate:

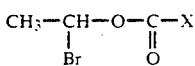

According to European Patent Application EP 108, 547, a free radical bromination of ethyl chloroformate or of ethyl bromoformate is carried out.

This free radical bromination has disadvantages. The UV lamps employed in preference to free radical initiators consume large amounts of energy and the amount of energy consumed increases with increasing reaction periods used in implementing this method. Different brominated by-products are always obtained.

It is also possible to prepare 1-bromoethyl bromoformate by reacting acetaldehyde with bromophosgene as described in French Patent Application FR 2,532,933. However, in this case, it is essential to use catalysts, and bromophosgene is not a reagent which is available on the market. It is not very stable and is very difficult to prepare. It is manufactured, for example, by reacting carbon monoxide with bromine, but this reaction requires very specific industrial plants.

Another process for the preparation of 1-bromoethyl ethyl carbonate consists in brominating diethyl carbonate by the free radical method. The same disadvantages of the free radical methods as described above are encountered: production of by-products and high energy requirement. Additionally, this process cannot be suitable for the production of a number of 1-bromoethyl carbonates because, depending on the structure of the carbonate used as the starting material, bromine will be attached in a larger quantity with the hydrocarbon group other than the ethyl group; for example, when the attachment of bromine to ethyl isopropyl carbonate is attempted, ethyl 1-bromoisopropyl carbonate is the preponderant product obtained.

It is also possible to use 1-chloroethyl ethyl carbonate as the starting material and to carry out a substitution of chlorine by bromine using a large excess of a bromine salt such as lithium or ammonium bromide, as mentioned in European Patent Application No. 108,547. This method also has disadvantages because, as this is an equilibrium reaction, the reaction is incomplete.

For example, as mentioned in Example 12 of this application, with a 300% excess of lithium bromide, a mixture of brominated carbonate and 35% of 1-chloroethyl ethyl carbonate, and not the pure product, is obtained and the separation of the alpha-chlorinated carbonate and the alpha-brominated carbonate is very difficult, as in the case of all other lower alkyl carbonates.

A new process for the preparation of 1-bromoethyl hydrocarbyl carbonates has very recently been proposed in French Patent N° 2 573 756. According to this process, hydrobromic acid is added to a vinyl hydrocarbyl carbonate; however, this process does not make it possible to obtain alpha-brominated carbonates other than 1-bromoethyl carbonates, and vinyl chloroformate which is useful in the preparation of the carbonate used as the starting material is not very easy to obtain.

Consequently, there was a need for a new process for the preparation of a large variety of 1-bromoalkyl hydrocarbyl carbonates, which does not have the disadvantages described above.

The object of the invention is precisely to provide such a process.

According to this new process, 1-bromoalkyl hydrocarbyl carbonates, of formula:

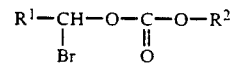

in which $R^1$ represents a straight-chain or branched, $C_1$-$C_{20}$ aliphatic or $C_5$-$C_{15}$ alicyclic radical and $R^2$ represents a substituted or unsubstituted, $C_1$-$C_{12}$ aliphatic, $C_5$-$C_{20}$ alicyclic or $C_6$-$C_{14}$ aromatic radical, are prepared by reacting an alpha-chlorinated carbonate of formula

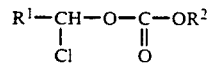

in which $R^1$ and $R^2$ have the above meanings, with an anhydrous compound of formula ZBr in which Z represents a hydrogen atom, the group $(CH_3)_3$-Si- or

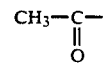

and may also represent a bromine atom when $R^2$ is other than an aromatic radical, in the presence of a catalyst chosen from amongst heteroaromatic amines, quaternary ammonium or phosphonium halides, hexasubstituted guanidium halides, alkali metal halides in combination with a complexing agent for their cation or alkaline earth metal halides, in a quantity of between 0.5 and 10 mole per cent relative to the alpha-chlorinated carbonate and at a temperature of between 40° C. and 150° C.

The reaction scheme is as follows:

$$R^1\underset{\underset{Cl}{|}}{C}H-O-\underset{\underset{O}{\|}}{C}-OR^2 + ZBr \xrightarrow{\text{catalyst}}$$

$$R^1\underset{\underset{Br}{|}}{C}H-O-\underset{\underset{O}{\|}}{C}-OR^2 + ZCl$$

The alpha-chlorinated carbonates used as the starting material are available on the market or may be prepared by known methods, for example by reacting alpha-chlorinated chloroformates with alcohols or phenols as mentioned in the Patent Applications FR 2 559 764 and EP 185,578.

The radical $R^1$ is preferably a $C_1$-$C_8$ aliphatic or a $C_5$-$C_{10}$ alicyclic radical.

$R^2$ is preferably a substituted or unsubstituted, $C_1$-$C_8$ aliphatic, $C_5$-$C_{10}$ alicyclic or $C_6$-$C_{10}$ aromatic radical.

The substituent(s) for $R^2$ is (are) preferably chosen from the group comprising aryl, aryloxy and alkoxy radicals and chlorine, fluorine and bromine atoms.

The compound ZBr must be anhydrous. It is generally employed in a quantity of between 1 and 2 moles per mole of alpha-chlorinated carbonate, preferably between 1.1 and 1.5 moles.

HBr, $(CH_3)_3$-Si-Br or $$CH_3-\underset{\underset{O}{\|}}{C}-Br$$

is preferably employed as the compound ZBr.

A catalyst is essential for obtaining high yields.

Pyridine, 4-dimethylaminopyridine, quaternary ammonium or phosphonium chlorides and bromides, hexabutylguanidinium chloride, potassium chloride in combination with 18-crown-6 crown ether and magnesium bromide may be mentioned as examples of catalysts.

The quantities of catalysts employed are preferably between 1 and 5 mole per cent relative to the quantity of the alpha-chlorinated carbonate.

The reaction mixture is generally heated and preferably to a temperature of between 60° and 120° C.

The reaction may be carried out with or without a solvent. Aromatic solvents such as toluene and aliphatic solvents such as 2-bromobutane or ethyl acetate may be mentioned as solvents which are well suited.

The process of the invention is simple. The implementation thereof does not require expensive plants or the use of high amounts of energy. The raw materials are easily available. It enables many alpha-brominated carbonates, and especially alpha-brominated carbonates which could never be prepared previously, to be obtained with a high purity and with high yields.

The 1-bromoalkyl hydrocarbyl carbonates prepared according to the process of the invention are intermediates of synthesis which may, for example, advantageously replace their less reactive chlorinated homologues or more unstable iodinated homologues in many reactions.

One of their important applications is the modification the carboxylic acid groups by the introduction of a carbonate group, in various compounds. The reaction may be outlined as follows:

$$ZCOOH + R^1\underset{\underset{Br}{|}}{C}H-O-\underset{\underset{O}{\|}}{C}-O-R^2 \xrightarrow{\text{base}}$$

$$Z-\underset{\underset{O}{\|}}{C}-O-\underset{\underset{R^1}{|}}{C}H-O-\underset{\underset{O}{\|}}{C}-OR^2 + HBr$$

This application is described especially in U.S. Pat. No. 4,426,391 and in the Patent Applications EP 54,512, EP 108,547, FR 2,532,933 and FR 2,387,988.

Thus, according to the teaching of the French Patent Application No. 2,532,933, alpha-brominated carbonates find a preferential application as blocking agents for some antibiotics such as bac-ampicillin.

They may also react with phosphoric acid derivatives, as mentioned in the Patent Application DE 2,628,410:

$$\underset{R^5}{\overset{R^4O}{\diagdown}}\underset{X}{\overset{\|}{P}}-S-Z + Br-\underset{\underset{R^1}{|}}{C}H-O-\underset{\underset{O}{\|}}{C}-OR^2 \longrightarrow$$

$$\underset{R^5}{\overset{R^4O}{\diagdown}}\underset{X}{\overset{\|}{P}}-S-\underset{\underset{R^1}{|}}{C}H-O-\underset{\underset{O}{\|}}{C}-OR^2 + ZBr$$

The compounds obtained according to this reaction scheme find a useful application as insecticidal products.

As the C—Br bond is much more labile than the C—Cl bond, alpha-brominated carbonates could be used in a much smaller quantity than the corresponding alpha-chlorinated carbonates. The reaction conditions will be milder and a certain degradation of the starting compound will therefore be avoided. The yields will be higher.

Moreover, the alpha-brominated carbonates are much more stable than the corresponding iodinated carbonates and this will enable, when they are used for replacing them, products of higher purity to be obtained in a larger quantity.

The examples which follow illustrate the invention without, however, limiting it.

EXAMPLE 1

Preparation of 1-bromoethyl isopropyl carbonate 13.11 g (78.7 mmol) of alpha-chloroethyl isopropyl carbonate and 0.35 g (1.09 mmol; 0.014 eq.) of tetra-n-butylammonium bromide are introduced into a reactor equipped with a stirrer, a thermometer, a condenser and a gas inlet tube. The mixture is heated to 80° C. and a gas stream containing 38 g of anhydrous hydrobromic acid is passed through it over 6 hours.

The reaction medium is degassed with argon and distillation is carried out under reduced pressure.

13.63 g (yield: Yld=82%) of the carbonate expected, with the following characteristics, are thereby collected:

Boiling point 80°-83° C./18 mm Hg

IR D (C=O): 1760 cm$^{-1}$ $^1$H NMR (CDCl$_3$, δ ppm): 6.60 (q, J=6 Hz, 1 H); 4.91 (sept, J=6 Hz, 1 H); 2.00 (d, J=6 Hz, 3 H); 1.3 (d, J=6 Hz, 6 H).

EXAMPLE 2

Preparation of 1-bromoethyl ethyl carbonate

The catalyst $MgBr_2.(Et_2O)_x$ is prepared starting with 0.15 g (0.006 mol) of magnesium and 1.18 g (0.006 mol) of 1,2-dibromoethane in 10 ml of ether. When the magnesium is used up, the lower phase is added to 20.2 g (0.13 mol) of 1-chloroethyl ethyl carbonate. The mixture is heated to 60°–65° C. and 36.6 g (0.23 mol) of bromine is slowly introduced over 5 h.

After stirring for 20 h at 60° C., the mixture is allowed to cool, 25 ml of $CH_2Cl_2$ are added and washing is carried out with water and then with an aqueous $Na_2S_2O_3$ solution.

Drying over $MgSO_4$, filtration, concentration and distillation under reduced pressure are carried out and 11.2 g (yield=43%) of the carbonate expected are collected.

Boiling point: 62°–66° C./18 mm Hg
IR D (C=0): 1760 cm$^{-1}$
$^1$H NMR (CDCl$_3$, δ ppm): 6.58 (q, J=6 Hz, 1 H); 4.20 (q, J=7 Hz, 2 H); 1.97 (d, J=6 Hz, 3 H); 1.30 (t, J=7 Hz, 3 H)

EXAMPLES 3 AND 4

Preparation of 1-bromoethyl ethyl carbonate and of 1-bromopentyl methyl carbonate The reaction is carried out as in Example 1. The reagents employed and the results obtained are given in the table below:

EXAMPLE 5

Preparation of 1-bromoethyl phenyl carbonate 15.4 g (0.077 mol) of 1-chloroethyl phenyl carbonate, 0.44 g (0.0014 mol) of tetrabutylammonium bromide and 13.7 g (0.090 mol) of trimethylsilane bromide are introduced into a distillation apparatus equipped with a 15 cm Vigreux column, a thermometer and a stirrer. The mixture is heated at 90° C. for 24 h and the trimethylsilane chloride released is removed by distillation. The product expected is then distilled. 17.2 g (Yld=91%) are obtained.

Boiling point: 72°–77° C./0.04 mm Hg
IR D (C=0) 1775 cm$^{-1}$
$^1$H NMR (CDCl$_3$, δ ppm); 7.6–6.9 (m, 5 H); 6.56 (q, J=6 Hz, 1 H); 1.98 (d, J=6 Hz, 3 H)

EXAMPLES 6 TO 8

Preparation of 1-bromoethyl ethyl carbonate

The reaction is carried out as in Example 5 starting with 1-chloroethyl ethyl carbonate in the presence of various catalysts and replacing the trimethylsilane bromide with acetyl bromide. The quantities of free agents employed and the results obtained are given in the table below.

| EX. | Cl<br>\|<br>RCHOCOR'<br>\|\|<br>O | Catalyst | HBr | T° C. | Period | Yld |
|---|---|---|---|---|---|---|
| 3 | Cl<br>\|<br>CH$_3$CHOCOCH$_2$CH$_3$<br>\|\|<br>O<br>37.4 g; 0.245 mol | MgBr$_2$.(Et$_2$O)$_x$$^b$<br>0.0093 mol | 35.1 g;<br>0.434 mol | 70° C. | 24 h | 76% |
| 4 | Cl O<br>\| \|\|<br>C$_4$H$_9$CHOCOCH$_3$<br>30.5 g; 0.169 mol | 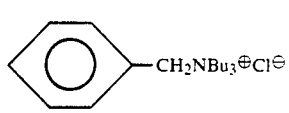—CH$_2$NBu$_3$⊕Cl⊖<br>1.0 g; 0.003 mol | 19.4 g;<br>0.24 mol | 80–<br>85° C. | 7 h | 34%$^a$ |

$^a$non-optimized yield
$^b$MgBr$_2$.(Et$_2$O)$_x$ prepared starting with Mg + BrCH$_2$CH$_2$Br in ether as in Example 2.

| EX | Cl<br>\|<br>CH$_3$CHOCOEt<br>\|\|<br>O | Catalyst | CH$_3$—C—Br<br>\|\|<br>O | T° C. | Period | Br<br>\|<br>CH$_3$CHOCOEt<br>\|\|<br>O<br>Yield |
|---|---|---|---|---|---|---|
| 6 | 20.5 g;<br>0.13 mol | (C$_8$H$_{17}$)$_3$NMe⊕Cl⊖<br>0.67 g;<br>0.0017 mol | 19.7 g;<br>0.16 mol | 100–<br>105 | 26 h | 73% |

| EX | CH₃CHOCOEt (Cl) | Catalyst | CH₃—C—Br (O) | T° C. | Period | Yield |
|----|------|----------|------|------|--------|-------|
| 7 | 20.1 g; 0.13 mol | 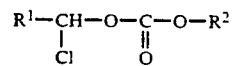 N<br>0.50 g; 0.006 mol | 21.6 g; 0.18 mol | 95 | 24 h | 63% |
| 8 | 20.1 g; 0.13 mol | KCl - 18-C-6<br>0.80 g; 0.011 mol<br>1.20 g; 0.0045 mol | 20.4 g; 0.17 mol | 95 | 24 h | 55% |

EXAMPLE 9

Preparation of 1-bromoethyl isopropyl carbonate 35.2 g (0.21 mol) of 1-chloroethyl isopropyl carbonate, 0.71 g (0.0022 mol) of tetrabutylammonium bromide and 40 ml of 2-bromobutane are introduced into an apparatus equipped with a thermometer, a stirrer and a Soxhlet extractor filled with $CaCl_2$ and fitted with a condenser cooled by dry ice and ethyl acetate (in order to recycle the excess HBr) and a gas inlet tube from above.

The mixture is heated to 95°-104° C. and a gas stream containing 26.1 g (0.32 mol) of anhydrous hydrobromic acid is passed through it over 8 hours.

The reaction medium is degassed with argon, the 2-bromobutane is removed, distillation is carried out under reduce-d pressure and 40 g of the product expected are obtained (Yld=90%).

Boiling point: 82°/18 mm Hg

EXAMPLE 10

Preparation of 1-bromoethyl isopropyl carbonate

A solution of 1-chloroethyl isopropyl carbonate (16.7 g; 0.10 mol) and hexabutylguanidinium chloride (0.43 g; 0.0011 mol) in toluene (40 ml) is heated to 115° C. and a gas stream containing 15 g (0.186 mol) of anhydrous hydrobromic acid is passed through it over 7 hours.

The reaction medium is degassed with argon, the toluene is removed, the product is distilled under reduced pressure and 16.0 g of the expected product is obtained (Yld=76%).

We claim:

1. Process for the preparation of 1-bromoalkyl carbonates of the formula:

$$R^1-CH-O-C-O-R^2$$
$$\quad\;\;| \qquad \;\;\|$$
$$\;\;\;Br \qquad O$$

in which $R^1$ represents a straight-chain or branched, $C_1$-$C_{20}$ aliphatic or $C_5$-$C_{15}$ alicyclic radical and $R^2$ represents a $C_1$-$C_{12}$ aliphatic, $C_5$-$C_{20}$ alicyclic or $C_6$-$C_{14}$ aromatic radical, unsubstituted or substituted by a member chosen from the group consisting of aryl, aryloxy, alkoxy, chlorine, fluorine, and bromine, by reacting an alpha-chlorinated carbonate of the formula:

$$R^1-CH-O-C-O-R^2$$
$$\quad\;\;| \qquad \;\;\|$$
$$\;\;\;Cl \qquad O$$

in which $R^1$ and $R^2$ have the above meanings, with anhydrous hydrobromic acid in the presence of a catalyst wherein the catalyst is chosen from the group consisting of tertiary aromatic heterocyclic amines, quaternary ammonium or phosphonium halides, hexasubstituted guanidinium halides, alkali metal halides in combination with 18-crown-6 crown ether and alkaline earth metal halides, in a quantity of between 0.5 and 10 mole percent relative to the alpha-chlorinated carbonate and at a temperature of between 40° and 150° C.

2. Process according to claim 1, wherein $R^1$ represents a $C_1$-$C_8$ aliphatic or $C_5$-$C_{10}$ alicyclic radical.

3. Process according to claim 2, wherein $R^2$ represents a substituted or unsubstituted, $C_1$-$C_8$ aliphatic, $C_5$-$C_{10}$ alicyclic or $C_6$-$C_{10}$ aromatic radical.

4. Process according to claim 2, wherein the hydrobromic acid is employed in a quantity of between 1.05 and 2 moles per mole of the alpha-chlorinated carbonate.

5. Process according to claim 4, wherein the hydrobromic acid is employed in a quantity of between 1.1 and 1.5 moles per mole of the alpha-chlorinated carbonate.

6. Process according to claim 2, wherein the catalyst is employed in a quantity of between 1 and 5 mole (%) percent relative to the quantity of alpha-chlorinated carbonate.

7. Process according to claim 2, wherein the catalyst employed is chosen from the group consisting of pyridine, 4-dimethylaminopyridine, quaternary ammonium or phosphonium chlorides and bromides, hexabutylguanidinium chloride, potassium chloride in combination with 18-crown-6 crown ether and magnesium bromide.

8. Process according to claim 2, wherein the reaction temperature is between 60° and 120°.

9. Process according to claim 2, wherein the reaction is carried out in the presence of a solvent.

10. Process according to claim 9, wherein the solvent is chosen from the group consisting of aromatic solvents and aliphatic solvents.

11. Process for the preparation of 1-bromoalkyl carbonates of the formula:

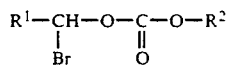

in which $R^1$ represents a straight-chain or branched, $C_1$-$C_{20}$ aliphatic or $C_5$-$C_{15}$ alicyclic radical and $R^2$ represents a $C_1$-$C_{12}$ aliphatic, $C_5$-$C_{20}$ alicyclic or $C_6$-$C_{14}$ aromatic radical, unsubstituted or substituted by a member chosen from the group consisting of aryl, aryloxy, alkoxy, chlorine, fluorine, and bromine, wherein alpha-chlorinated carbonate of formula:

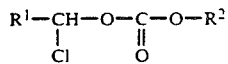

in which $R^1$ and $R^2$ have the above meanings is reacted with an anhydrous compound of formula ZBr in which Z represents the groups $(CH_3)_3$-Si- or

and, when $R^2$ is other than an aromatic radical, Z also represents a bromine atom, in the presence of a catalyst chosen from the group consisting of tertiary aromatic heterocyclic amines, quaternary ammonium or phosphonium halides, hexasubstituted guanidinium halides, alkali metal halides in combination with 18-crown-6 crown ether and alkaline earth metal halides, in a quantity of between 0.5 and 10 mole percent relative to the alpha-chlorinated carbonate and at a temperature of between 40° and 150° C.

12. Process according to claim 11, wherein $R^1$ represents a $C_1$-$C_8$ aliphatic or $C_5$-$C_{10}$ alicyclic radical.

13. Process according to claim 12, wherein $R^2$ represents a substituted or unsubstituted, $C_1$-$C_8$ aliphatic, $C_5$-$C_{10}$ alicyclic or $C_6$-$C_{10}$ aromatic radical.

14. Process according to claim 12, wherein the hydrobromic acid is employed in a quantity of between 1.05 and 2 moles per mole of the alpha-chlorinated carbonate.

15. Process according to claim 14, wherein the compound ZBr is employed in a quantity of between 1.1 and 1.5 moles per mole of the alpha-chlorinated carbonate.

16. Process according to claim 12, wherein the alpha-chlorinated carbonate is reacted with $(CH_3)_3$-Si-Br or

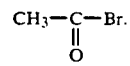

17. Process according to claim 12, wherein the catalyst is employed in a quantity of between 1 and 5 mole (%) percent relative to the quantity of alpha-chlorinated carbonate.

18. Process according to claim 12, wherein the catalyst employed is chosen from the group consisting of pyridine, 4-dimethylaminopyridine, quaternary ammonium or phosphonium chlorides and bromides, hexabutylguanidinium chloride, potassium chloride in combination with 18-crown-6 crown ether and magnesium bromide.

19. Process according to claim 12, wherein the reaction temperature is between 60° and 120°.

20. Process according to claim 12, wherein the reaction is carried out in the presence of a solvent.

21. Process according to claim 20, wherein the solvent is chosen from the group consisting of aromatic solvents and aliphatic solvents.

* * * * *